US005581346A

United States Patent [19]
Sopori

[11] Patent Number: 5,581,346
[45] Date of Patent: Dec. 3, 1996

[54] SYSTEM FOR CHARACTERIZING SEMICONDUCTOR MATERIALS AND PHOTOVOLTAIC DEVICE

[75] Inventor: Bhushan L. Sopori, Denver, Colo.

[73] Assignee: Midwest Research Institute, Kansas City, Mo.

[21] Appl. No.: 314,201

[22] Filed: Sep. 28, 1994

Related U.S. Application Data

[63] Continuation-in-part of Ser. No. 60,301, May 10, 1993, Pat. No. 5,406,367.

[51] Int. Cl.[6] ........................................ G01N 21/88
[52] U.S. Cl. ...................... 356/30; 356/237; 356/446
[58] Field of Search .......................... 356/30, 31, 237, 356/445, 446, 447, 448, 236, 371

[56] References Cited

U.S. PATENT DOCUMENTS

| | | | |
|---|---|---|---|
| 4,243,473 | 1/1981 | Yamaguchi et al. | 156/626 |
| 4,329,052 | 5/1982 | Colombo et al. | 356/335 |
| 4,482,245 | 11/1984 | Makabe et al. | 356/30 |
| 4,626,101 | 12/1986 | Ogawa et al. | 356/237 |
| 4,794,265 | 12/1988 | Quackenbos et al. | 250/572 |
| 4,840,487 | 6/1989 | Noguchi et al. | 356/355 |
| 4,925,298 | 5/1990 | Dobrilla | 356/30 |
| 5,008,542 | 4/1991 | Look et al. | 250/341 |

FOREIGN PATENT DOCUMENTS

| | | | |
|---|---|---|---|
| 3-214043 | 9/1991 | Japan | 356/448 |

OTHER PUBLICATIONS

B. L. Sopori, Use of Optical Scattering to Characterize Dislocations in Semiconductors, 22 Appl. Optics 4676 (1988).

B. L. Sopori, "A New Etch for Polycrystalline Silicon," J.Electrochem. Soc.: Solid–State Science and Technology, vol. 131. No. 3, p. 667 (1984).

*Primary Examiner*—F. L. Evans
*Attorney, Agent, or Firm*—Edna M. O'Connor

[57] ABSTRACT

Apparatus for detecting and mapping defects in the surfaces of polycrystalline material in a manner that distinguishes dislocation pits from grain boundaries includes a first laser of a first wavelength for illuminating a wide spot on the surface of the material, a second laser of a second relatively shorter wavelength for illuminating a relatively narrower spot on the surface of the material, a light integrating sphere with apertures for capturing light scattered by etched dislocation pits in an intermediate range away from specular reflection while allowing light scattered by etched grain boundaries in a near range from specular reflection to pass through, and optical detection devices for detecting and measuring intensities of the respective intermediate scattered light and near specular scattered light. A center blocking aperture or filter can be used to screen out specular reflected light, which would be reflected by nondefect portions of the polycrystalline material surface. An X-Y translation stage for mounting the polycrystalline material and signal processing and computer equipment accommodate raster mapping, recording, and displaying of respective dislocation and grain boundary defect densities. A special etch procedure is included, which prepares the polycrystalline material surface to produce distinguishable intermediate and near specular light scattering in patterns that have statistical relevance to the dislocation and grain boundary defect densities. A reflectance measurement of the piece of material is obtained by adding together the signals from the optical detection devices. In the case where the piece of material includes a photovoltaic device, the current induced in the device by the illuminating light can be measured with a current sensing amplifier after the light integrating sphere is moved away from the device.

25 Claims, 14 Drawing Sheets
(5 of 14 Drawing(s) in Color)

F I G. 10a
F I G. 10b

SYSTEM FOR CHARACTERIZING SEMICONDUCTOR MATERIALS AND PHOTOVOLTAIC DEVICE

CONTRACTUAL ORIGIN OF THE INVENTION

The United States Government has rights in this invention under Contract No. DE-AC36-83CH10093 between the U.S. Department of Energy and the National Renewable Energy Laboratory, a Division of Midwest Research Institute.

This application is a continuation-in-part of Ser. No. 08/060,301, filed on May 10, 1993, entitled "Improved Defect Mapping System" now U.S. Pat. No. 5,406,367.

BACKGROUND OF THE INVENTION

1. Field of the Invention

This invention is related generally to improve techniques for mapping defects on semiconductor surfaces and characterizing photovoltaic devices and more particularly to an improved optical system that can more effectively distinguish dislocation pits from grain boundaries in mapping polycrystalline devices surfaces and that can produce maps of the internal photoresponse of photovoltaic devices by using data from maps produced of the reflectance and external photoresponse of photovoltaic devices.

2. Description of the Prior Art

The quality and suitability of single crystalline and polycrystalline materials, such as silicon, gallium-arsenic, and others, for use as substrates for semiconductor applications are affected by defects, such as dislocations, in the crystalline structures. Generally, higher densities of dislocations are indicative of lower quality materials. Therefore, there is a need for systems to detect, measure, and map dislocation densities in single crystalline and polycrystalline materials for purposes of analysis and quality control.

There are a number of systems that have been developed to detect and map dislocation densities. The methods used most commonly in the industry currently utilize a surface cleaning or polish step followed by some variation of an etch, which reveals dislocations that intersect the surface of the material by forming a pit at each dislocation site. The pits can then be detected, counted, and mapped, and the density of the pits, i.e., number of pits per unit of surface area, can be determined. This etch pit density (EPD) is considered by persons skilled in this art to be a reliable indicator of the number and density of dislocations in the substrate, and the pits have patterns that reflect slip planes in the crystal lattice of the material.

The most commonly used method of detecting and counting pits to determine EPD is visual observation through a microscope and counting. This process is obviously labor intensive, time consuming, and tedious work. Some alternative systems based on optical technologies to detect and map EPDs have been developed that apparently work on monocrystalline substrates, but none that work reliably for polycrystalline substrates. For example, the U.S. Pat. No. 4,925,298, issued to P. Dobrilla, compares specularly reflected light from an etched sample surface to light reflected from a reference surface to determine EPD. U.S. Pat. No. 5,008,542, issued to D. Look et al. is similar, except it detects light transmitted through the substrate rather than reflected light. In both of those techniques, the specular light is detected, so increase of dislocation density results in increase of scattered light, thus decrease in detection signal. However, polycrystalline substrates present major problems for those systems, because grain boundaries cause substantial light scattering, thus affecting light detection signals and skewing EPD measurements.

It has also been shown and is now well-known in the industry that light scattering from a defect-etched surface can be used to determine surface dislocation numbers statistically. In fact, as reported in B. L. Sopori, "Use of Optical Scattering to Characterize Dislocations in Semiconductors," 22 APPL OPTICS 4676 (1988), it has been determined that the total integrated light scattered from an illuminated region of a defect-etched surface is proportional to the number of dislocation etch pits in that area, provided that the surface is etched for defect delineation. A light integrating sphere positioned on the surface of the material collects and integrates substantially all of the scattered light, and a photodetector mounted in the integrating sphere measures the integrated light intensity, thus the extent of EPD in an illuminated area on the surface. Again, however, while that large beam statistical EPD detection and mapping technique works well for many applications involving single crystalline materials, it does not work well with polycrystalline structures. Grain boundaries in polycrystalline materials are "grooved" in the defect etching process required for defect delineation, so scattering of light by the grain boundaries can cause a larger amplitude integrated light in the integrating sphere, thus an erroneous EPD signal.

Finally, at the present time there is no method known to provide maps of reflectance, external photoresponse, internal photoresponse, and other parameters relating to polycrystalline cells, such as efficiency of conversion, minority carrier diffusion length, and depth-dependent photoresponse. These maps can contribute valuable information on the effectiveness of the cell and also of the etching process.

SUMMARY OF THE INVENTION

A general object of this invention, therefor, is to provide an improved defect mapping system for crystalline materials.

Another general object of this invention is to provide a defect mapping system that is useable and accurate on polycrystalline materials as well as single crystalline materials.

A more specific object of this invention is to provide an optical scattering defect mapping system wherein light scattered by etched dislocation pits can be discriminated from light scattered by grain boundaries.

Another specific object of this invention is to provide an improvement to large beam statistical EPD detection and mapping systems that can be used on both single crystalline and polycrystalline materials.

An even more specific object of this invention is to provide an improved large beam statistical EPD detection and mapping system that can be adjusted to detect and map either EPD or grain boundaries of a polycrystalline material.

Another specific object of this invention is to provide an EPD mapping system that corrects for variations in etch pit size in polycrystalline material from sample to sample.

Another specific object of the present invention is to provide a detection and mapping system with an increased ability to distinguish between EPD and grain boundaries of a polycrystalline material.

Still another specific object of this invention is to provide a method for producing maps of different parameters of polycrystalline materials and devices, such as reflectance and photoresponse maps.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

To achieve the foregoing and other objects and in accordance with the purposes of the present invention, as embodied and broadly described therein, a defect mapping system includes a method for scattering light from the surface of a crystalline material that contains two types of defects, for example, dislocation defects and grain boundary defects, such that the first type of defect scatters light in a first pattern, and the second type of defect scatters light in a second pattern by using two different light beams. The light for detecting the first type of defect is provided by a relatively wide beam having a relatively long wavelength. The light for detecting the second type of defect is provided by a relatively narrow beam having a relatively short wavelength. The light of the first pattern is captured in a light integrating sphere for detection. The light of the second pattern is near specular and is passed through the light integrating sphere for separate detection.

Further, a mapping system includes the capability for generation of reflectance maps of photovoltaic devices or materials which are unimpeded by the extraneous scattered light collected by the light integrating sphere. Furthermore, the mapping system includes a capability to remove the light integrating sphere and the use of beams with different wavelengths to provide Light Beam Induced Current (LBIC) maps that represent different characterization parameters of the material/device. The data contained in the reflectance and the corresponding LBIC maps can be used to produce information relating to the internal parameters of the material/device.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The accompanying drawings, which are incorporated in and form a part of the specifications, illustrate the preferred embodiments of the present invention, and together with the descriptions serve to explain the principles of the invention.

In the Drawings:

FIG. 1 is a schematic diagram of the improved defect mapping system of the present invention;

FIG. 2 is an enlarged schematic illustration of the optical components of the system shown in FIG. 1;

FIG. 3a is a schematic representation of the scattered light rays from an illuminated crystalline material sample that has an etched surface to reveal and delineate defects, particularly dislocations, in the crystalline material;

FIG. 3b is a representation of a typical scattered light pattern from an illuminated crystalline sample that has been etched according to this invention;

FIG. 3c is an enlarged view of etch pits on the surface of a silicon sample, wherein the etch pits are substantially circular in shape;

FIG. 3d is a photograph of an actual light pattern that has been scattered by the surface of the silicon sample of FIG. 3c according to this invention;

FIG. 3e is an enlarged view of etch pits on the surface of a silicon sample, wherein the etch pits are substantially elliptical in shape;

FIG. 3f is a photograph of an actual light pattern that has been scattered by the surface of the silicon sample of FIG. 3e;

FIG. 3g is an enlarged view of etch pits on the surface of a silicon sample, wherein the etch pits are two different shapes (resembling ellipses);

FIG. 3h is a photograph of an actual light pattern that has been scattered by the surface of the silicon sample of FIG. 3g;

FIG. 4a is a schematic illustration of light rays scattered by a V-shaped etch grain boundary in a polycrystalline material;

Figure 2:
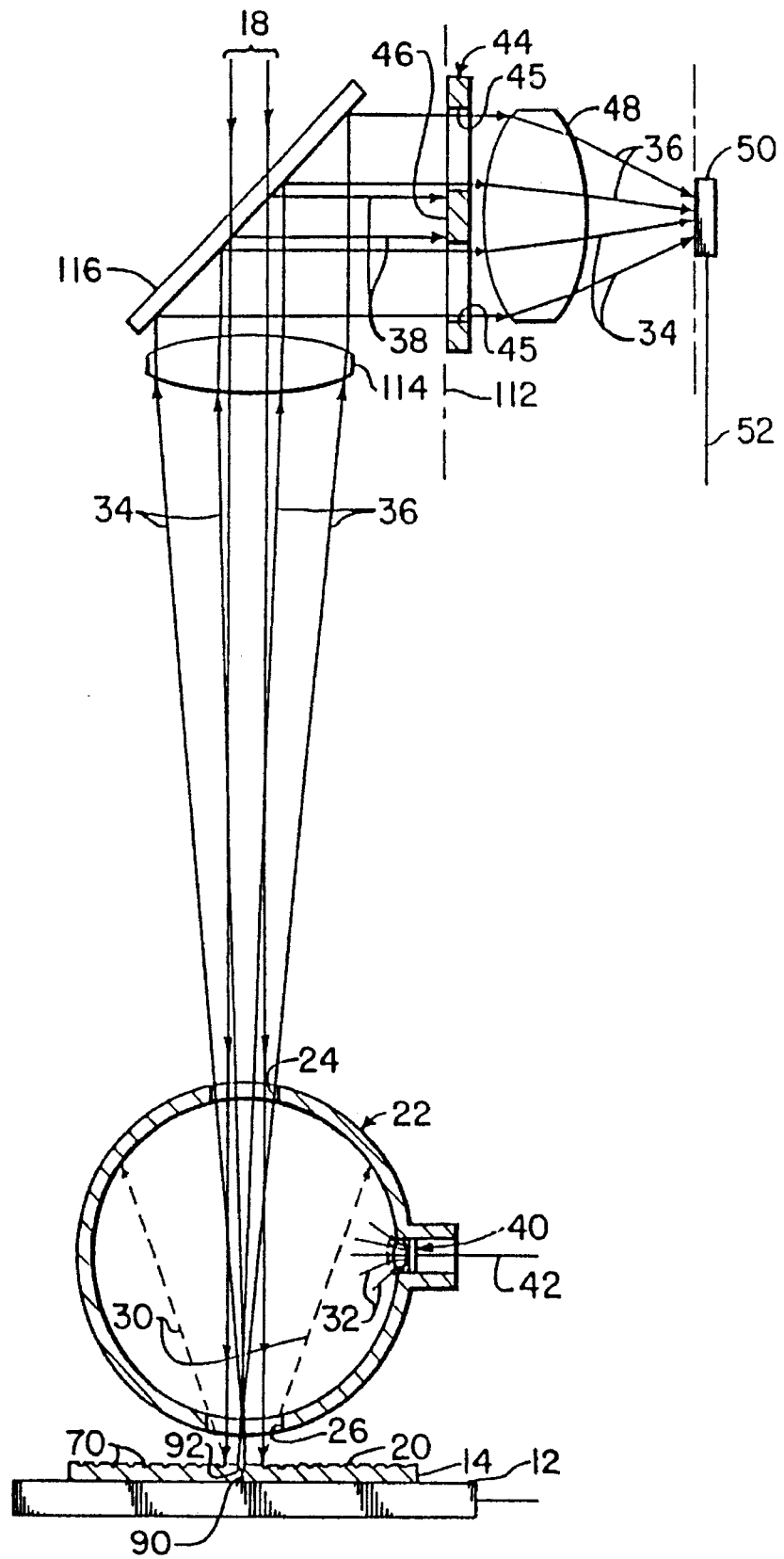
Figure 3B:
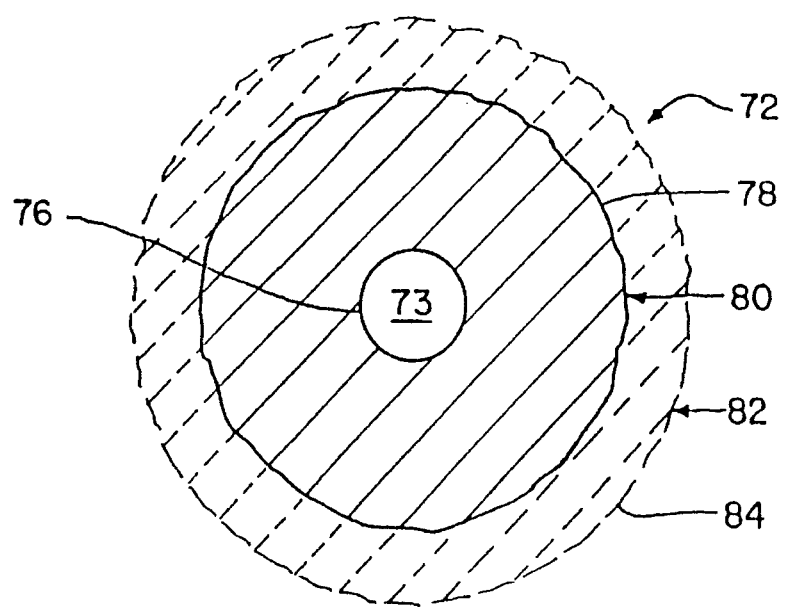
Figure 4B:
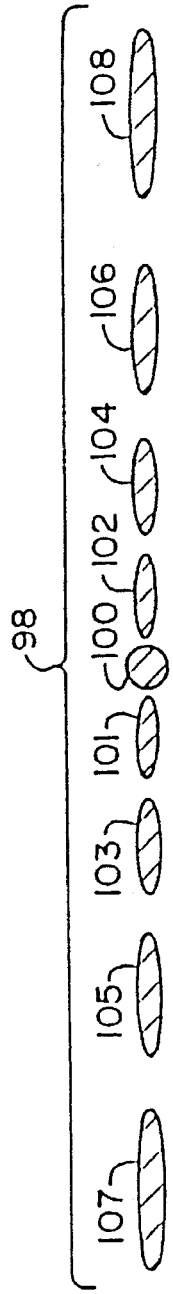
Figure 4A:
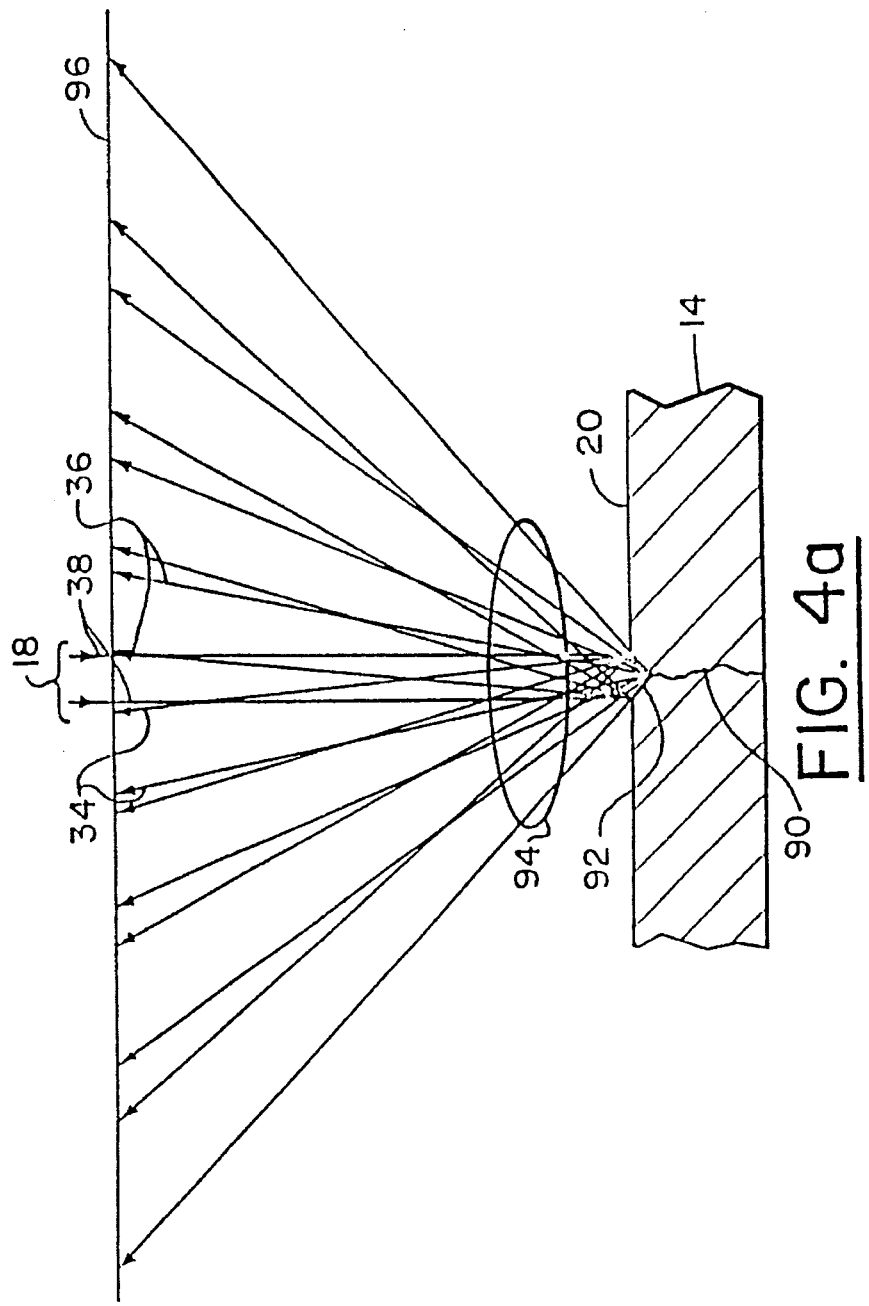
Figure 5:
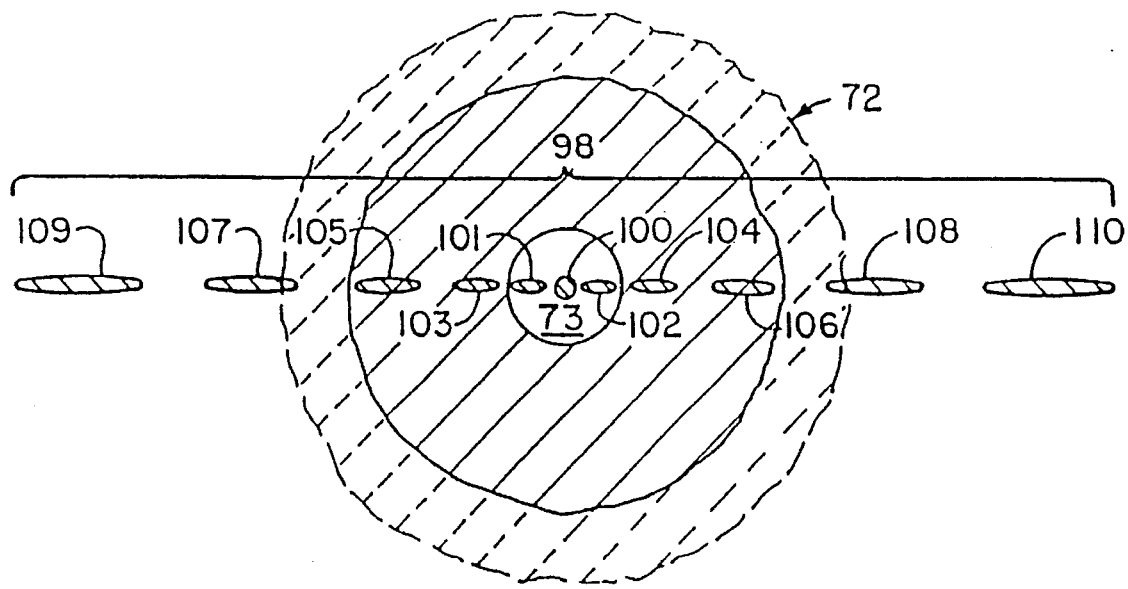
Figure 6:
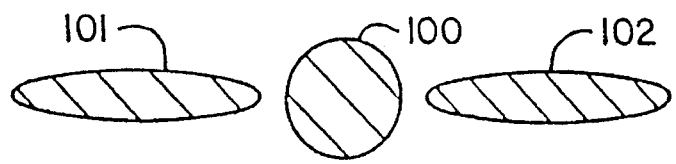
Figure 7:
Figure 8:
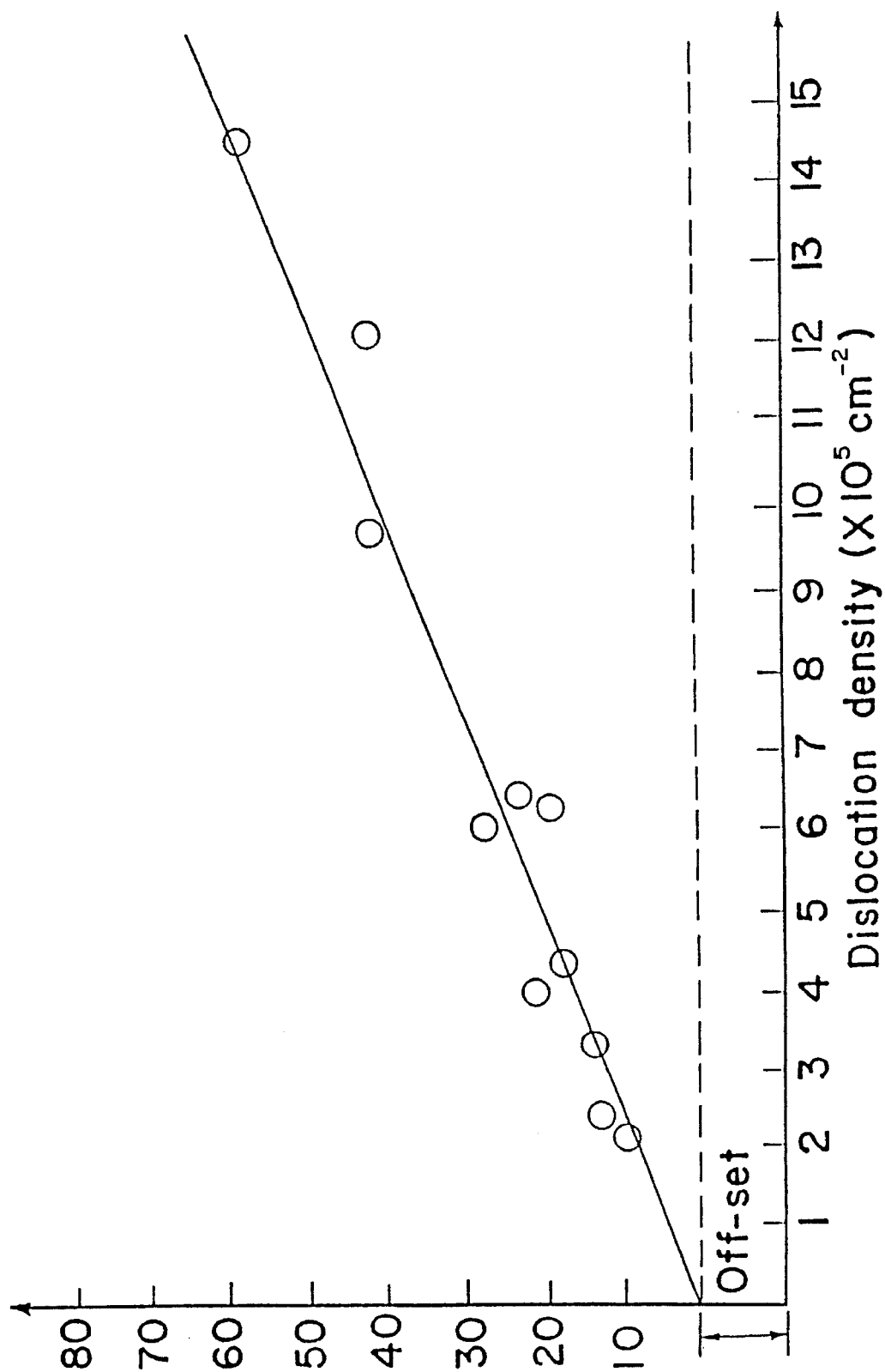
Figure 9:
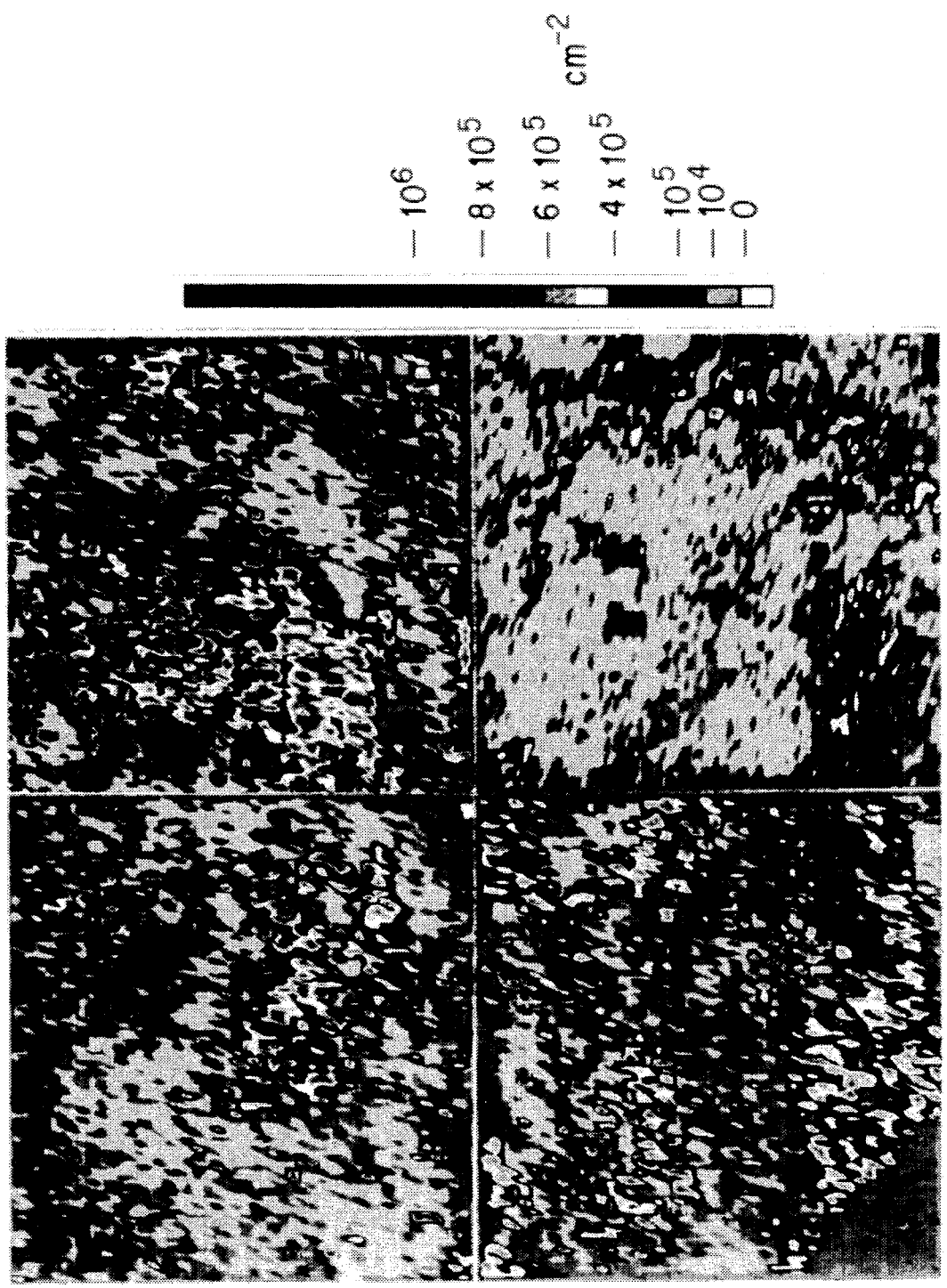
Figure 11:
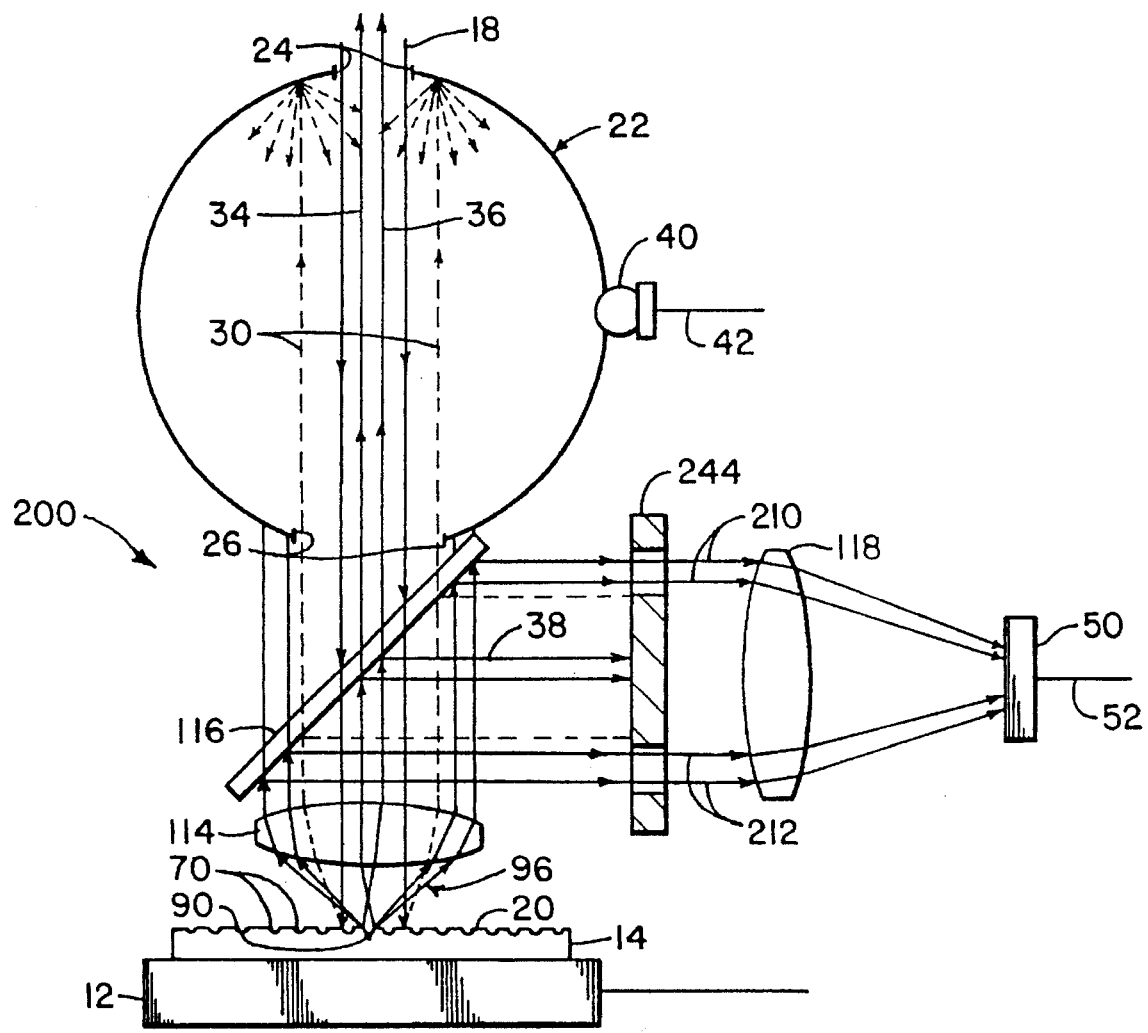
Figure 12:
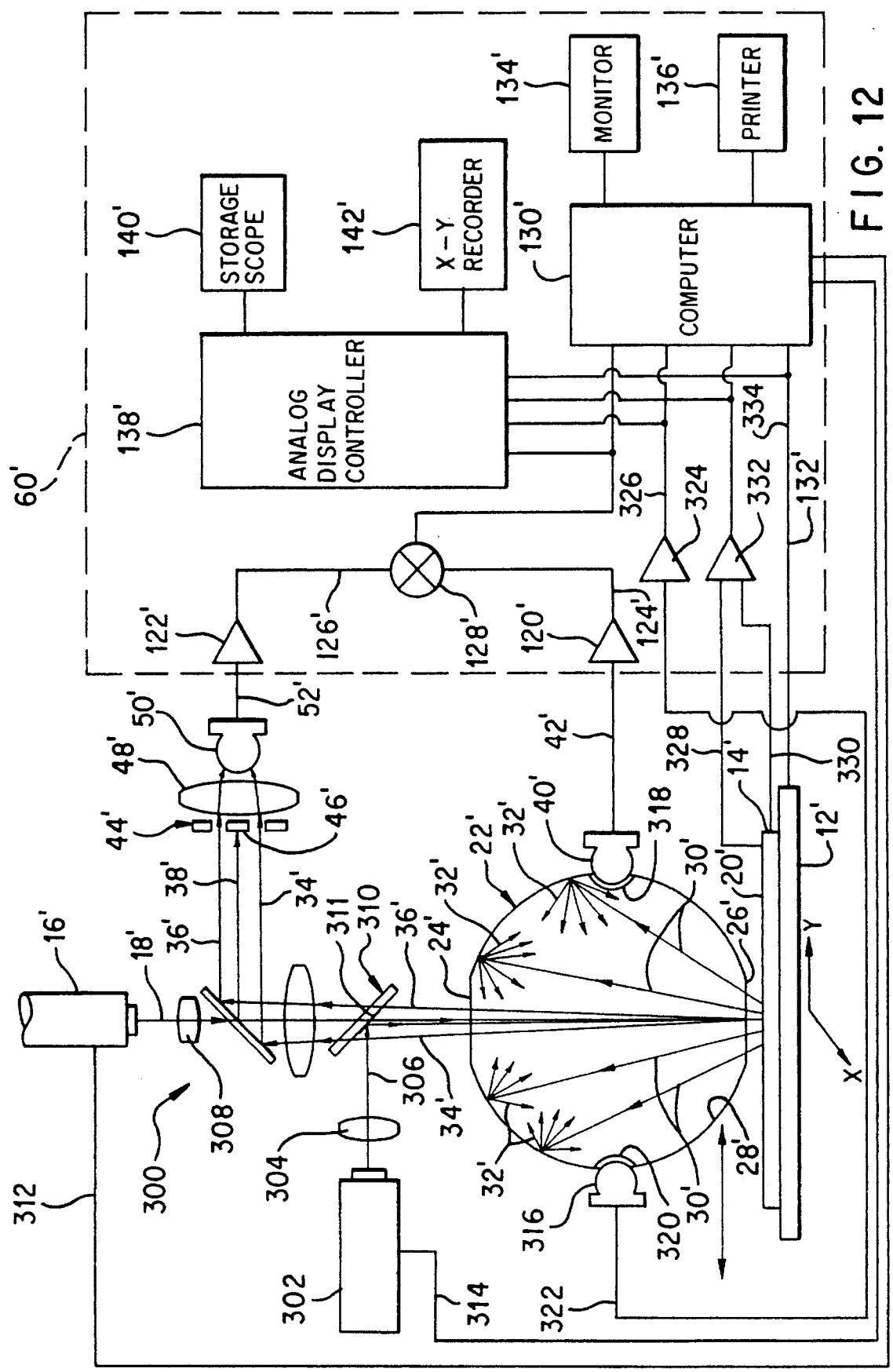
Figure 13:
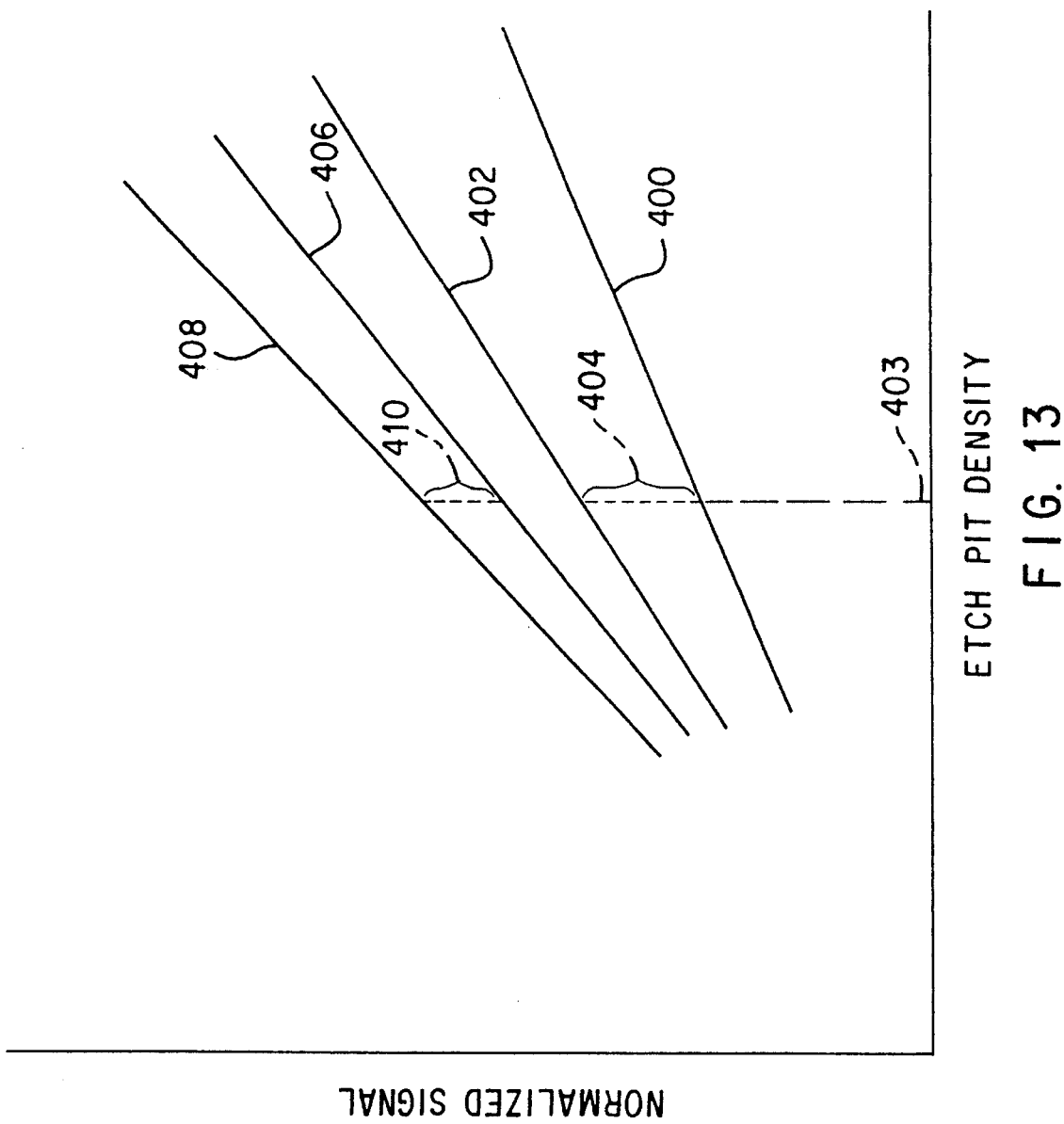

FIG. 4b is an illustration of the pattern of light scattered by a V-shaped etch grain boundary of FIG. 4a;

FIG. 5 illustrates the grain boundary light pattern of FIG. 4b superimposed on the etch pit light pattern of FIG. 3b, which combination occurs when a beam illuminating an etch pit sample surface encounters an etch grain boundary, as illustrated in FIG. 2;

FIG. 6 is an illustration of the central part of the grain boundary scattered light pattern that is captured separate from the etch pit scattered light according to this invention;

FIG. 7 is an illustration of the grain boundary scattered light pattern of FIG. 6 after removal of the center spot and converging for incidence on a photodetector;

FIG. 8 is a graph of detector signal intensity (integrated scattered light) plotted versus dislocation density;

FIG. 9 is a dislocation defect map of a crystal system wafer produced according to this process;

FIG. 10a is a photograph showing the grain boundaries in a surface of a polycrystalline silicon wafer;

FIG. 10b is a grain boundary defect map of the wafer of FIG. 10a produced according to this invention;

FIG. 11 is a schematic diagram of a second embodiment of a defect mapping system according to the present invention;

FIG. 12 is a schematic diagram of a third embodiment of a defect mapping system and a light beam induced current mapping system according to the present invention; and FIG. 13 is a graphical representation of the relationship between the normalized signal received from the diffuse light reflected from the material as a function of etch pit density at different wavelengths and for different etch pit sizes.

DETAILED DESCRIPTION OF THE PREFERRED EMBODIMENTS

Figure 1:
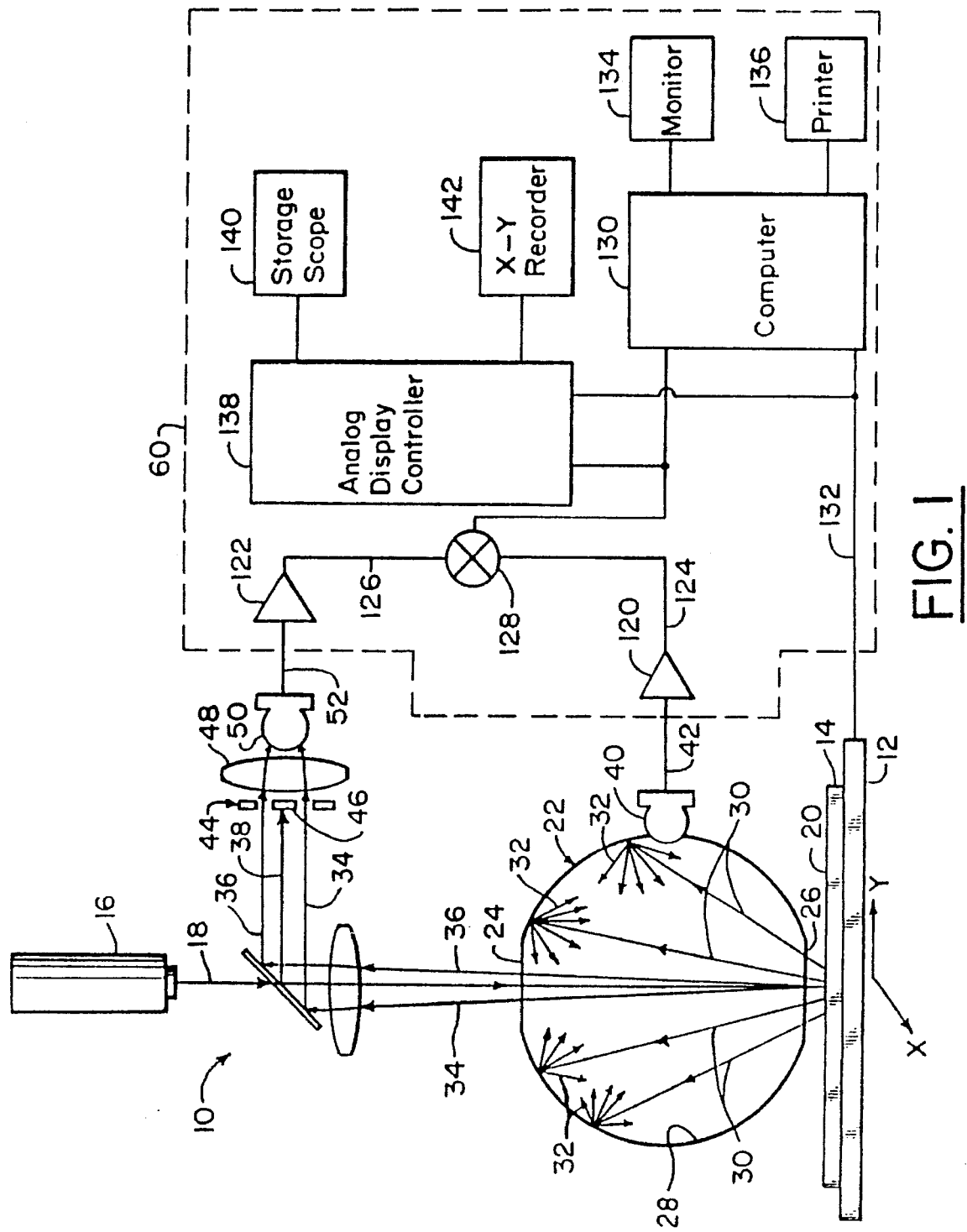

The improved defect mapping system 10 of this invention is illustrated schematically in FIG. 1. An X-Y translation stage 12 is provided for supporting a crystalline sample or substrate 14 positioned for defect detection and mapping according to this invention. A laser beam generator 16, such as a HeNe laser system capable of generating a laser beam 18 of light with a wavelength of approximately 6,382 Å, is positioned above the stage 12 and preferably oriented to direct a laser beam 18 perpendicularly onto the exposed surface 20 of crystalline material or sample 14.

A light integrating sphere 22, has two diametrically opposed apertures 24, 26 positioned to allow transmission of the laser beam 18 through the light integrating sphere 22, when it is positioned between the laser generator 16 and the sample 14. However, the light integrating sphere 22 captures light rays 30 that are scattered by the surface 20 of sample 14 through the bottom aperture 26. The interior surface 28 of the integrator 22 is coated with a material, such as magnesium oxide, that enhances uniform scattering and integrated distribution or diffusion of light rays 30 captured therein through the bottom aperture 26, as illustrated at 32. A first photodetector 40 positioned in the side of the light integrating sphere 22 detects the intensity of diffused light 32 in the light integrating sphere 22 and produces an analog signal on lead 42 indicative of the diffused light 32 intensity. As illustrated in the graph in FIG. 8, and as will be discussed in more detail below, the intensity of the diffused or integrated scattered light 32 in FIG. 1, thus the amplitude of the signal produced on lead 42, is a direct measure of etched pit dislocation density (EPD) on the position of surface 20 of sample 14 that is illuminated by laser beam 18.

At the same time, the near specular components 34, 36 of light scattered by etched grain boundaries (not shown in FIG. 1, but described below) in the surface 20 of a polycrystalline sample 14, along with specular light component 38, are allowed by bottom aperture 26 and top aperture 24 to pass through the light integrating sphere 22, as illustrated in FIG. 1. The specular light component 38, which is primary comprised of light reflected by smooth portions, i.e., nondefect portions, of the surface 20 of sample 14, is blocked and eliminated by an opaque center 46 of a center blocking aperture 44, while the near specular light components 34, 36 are passed to a convex converging lens 48 and to a second photodetector 50. Since most of the light that reaches this second photodetector 50 is the near specular component of light scattered by etched grain boundaries, as will be described in more detail below, a strong electric signal produced on lead 52 by photodetector 50 indicates the presence of a grain boundary in the portion of the surface 20 of sample 14 that is illuminated by the laser beam 18.

The signal processing and control unit 60 shown in FIG. 1 processes and stores the signals from the photodetectors 40 and 50 in conjunction with X-Y position information of the stage 12, as the stage 12 rasters the sample 14 under the laser beam 18. Therefore, visual displays or other outputs of etch pit density (EPD) or grain boundary mapping can be produced for all or any desired portion of the surface 20 of sample 14.

Figure 3A:
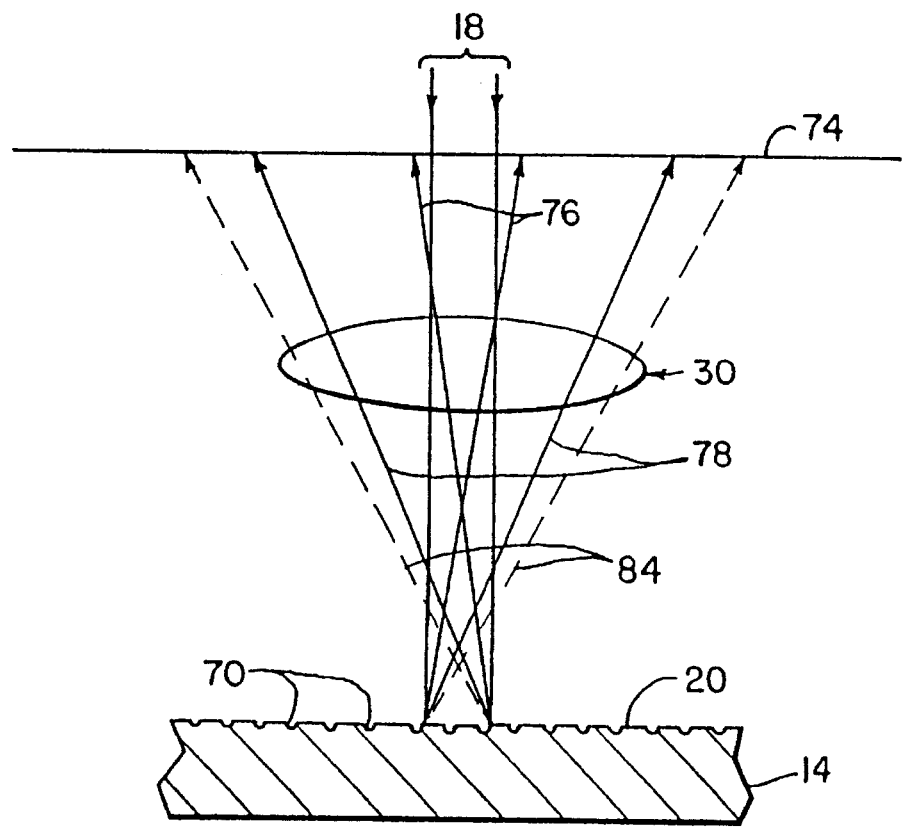

Referring now to FIGS. 3a and 3b, a crystalline sample 14 with etch pits 70 in the surface 20 where dislocation defects occur is shown illuminated by a laser beam 18. When properly etched, as will be described in more detail below, the etch pits 70 scatter the light in a definite and repeatable pattern 72 illustrated in FIG. 3b. The pattern 72 in FIG. 3b is the projection of the scattered light beams in FIG. 3a on the plane 74. Essentially, the etch pits 70 scatter most of the incident light from beam 18 in a conical pattern, as show in FIG. 3a, between about five degrees (5°) and twenty degrees (20°) from normal. The beams 76 illustrate the inner boundary of this range, and the beams 78 illustrate the outer boundary. Corresponding boundaries 76 and 78 define the primary high intensity light ring 80 of the resulting pattern 72 in FIG. 3b. A fringe ring 82 of less intensity surrounds the primary ring 80, as depicted by scattered fringe rays 84. The center circle 73 of pattern 72 is essentially devoid of scattered light from the etch pitted surface 20. All of the scattered light in the primary ring 80 and the fringe ring 82 of pattern 72 is collectively designated as the etch pit scattered light 30 for convenience in describing this invention.

Figure 3C:
Figure 3D:
Figure 3E:
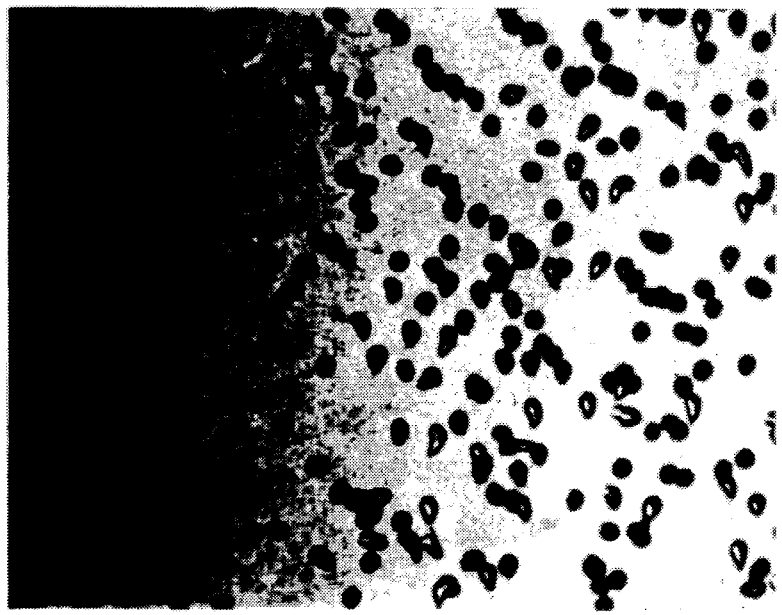
Figure 3F:
Figure 3G:
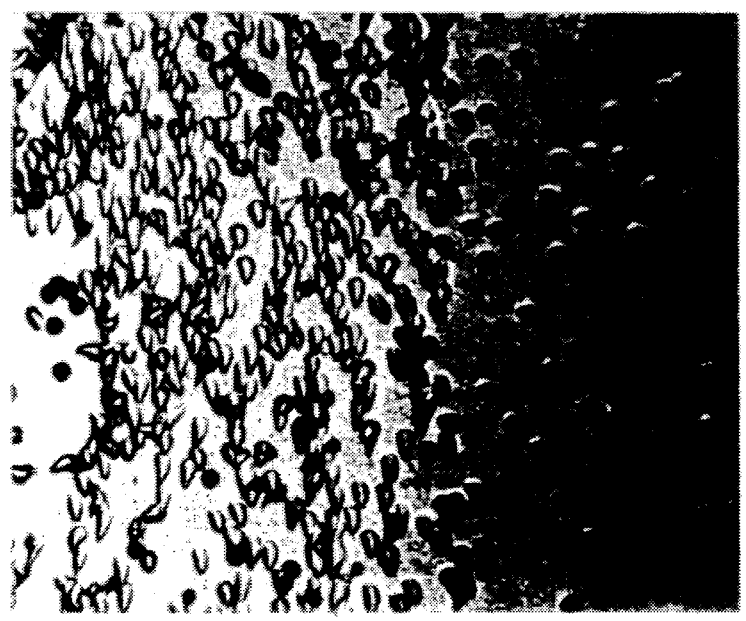
Figure 3H:

FIG. 3d is an illustration of a pattern 72 produced scattered light from the substantially circular shaped etch pits in FIG. 3c. Such circular shaped etch pits indicate dislocation defects that are oriented substantially normal to the surface, and, when etched as described below for this invention, will always produce the characteristic circular pattern of etch pit scattered light shown in FIG. 3d and depicted in FIG. 3b. In contrast, dislocation defects that are oriented oblique to the surface produce elliptical shaped etch pits, as shown in FIG. 3e. Such elliptical etch pits produce an elliptical shaped pattern of etch pit scattered light, as shown in FIG. 3f. A mixed set of etch pits comprising both circular and elliptical shapes in close proximity, as shown in FIG. 3g, will produce an irregular shaped etch pit scattered light pattern, as shown in FIG. 3h.

Referring now momentarily to FIGS. 1 and 2, the bottom aperture 26 of the light integrating sphere 22 is sized and positioned to admit most of the etch pit scattered light 30, for example, about 20 to 40 degrees from normal. The top aperture 24 is preferably sized and positioned to not allow light rays 30 scattered from the surface 20 wider than about five degrees from normal to pass therethrough. In other words, the top aperture 24 preferably coincides substantially with the void center circle 73 of the etch pit uttered light pattern 72 of FIG. 3b. Consequently, most of the etch pit uttered light 30 is captured and retained by light integrating sphere 22, where it is integrated to produce intense diffuse light 32 to induce a strong signal from photodetector 40. At the same time, very little of the etch pit uttered light 30 escapes through top aperture 24 to reach the second photodetector 50, so any signal produced by photodetector 50 is not influenced significantly by etch pit uttered light 30.

Referring now primary to FIGS. 4a and 4b, a grain boundary 90 in a polycrystalline material, when etched as described below, will produce a V-shaped groove 92 that is essentially one-dimensional and runs the length of the grain boundary 90 along the surface 20 of the sample 14. Light incident on such etch grain boundaries 90 is uttered in a substantially fan-shaped distribution 94 in a plane that is perpendicular to the surface 20. When the fan-shaped uttered light distribution 94 is projected onto a plane 96 that is parallel to surface 20, it forms a pattern, 98 of diverse elongated spots 101, 102, 103, 104, 105, 106, 107, 108 . . . as illustrated in FIG. 4b. The circular center spot 100 is substantially specular reflection or retroreflection from the V-shaped groove 92 or surface 20.

Referring again to FIG. 2, a polycrystalline sample 14 is illustrated on X-Y stage 12 with a grain boundary 90 and a V-shaped etch groove 92 where the grain boundary 90 intersects the surface 20, similar to that illustrated in FIG. 4a and described above. The surface 20 also has etch pits 70 where dislocations intersect the surface 20; however, the size and density proportions are not illustrated to scale because of limitations inherent in these kinds of illustrations for microscopic features. As shown in FIG. 2, a fairly wide or large diameter beam 18 is used to illuminate a sufficiently large portion of the surface 20 to obtain a good statistical sample of etch pits. Therefore, there is no attempt to focus the beam 18 to a point on the surface 20. In fact, it is preferred that a point focus is avoided. Generally, it is preferred to include at least two hundred etch pits in the illuminated area, which usually requires a beam 18 diameter of about 500 to 1,000 µm.

As also shown in FIG. 2 for purposes of illustrating additional features of this invention, the V-shaped grain boundary etch groove 92 is positioned in the area illuminated by beam 18. Consequently, both an etch pit scattered light pattern, such as one of the patterns illustrated in FIGS. 3a through 3h, and a grain boundary etch scattered light pattern, such as the pattern 98 illustrated in FIGS. 4a and 4b, are produced together. The result is a combination etch pit light scattered pattern, such as pattern 72 of FIGS. 3a and 3b, combined with a grain boundary etch pattern 98 of FIGS. 4a and 4b. The combination of these patterns 72 and 98 is illustrated in FIG. 5. The specular light components 38 of FIGS. 2 and 4a that produce center spot 100 of FIGS. 4b and 5, and the near specular light components 34 and 36 of FIGS. 2 and 4a that produce the inside spots 101 and 102, respectively, of FIGS. 4b and 5 deviate from specular normal for the most part less than five degrees (5°). Therefore, as best illustrated in FIGS. 2 and 5, those light components 34, 36, and 38 and their corresponding spots 100, 101, and 102 are for the most pan confined in the center area 73 that is substantially devoid of etch pit scattered light 30. Therefore, as shown in FIG. 2, the top aperture 24 of the light integrating sphere 22 allows the light components 34, 36 and 38 scattered or reflected by the grain boundary etch groove 92 to pass out of the light integrating sphere 22. Therefore, the limited pattern shown in FIG. 6 comprising only spots 100, 101, and 102 reach the plane 112 of the center block aperture 44 in FIG. 2. The specular light component 38 is subsequently blocked and eliminated from the system 10 by the center block aperture 44 as mentioned above. Consequently, only the near specular light components 34 and 36 scattered by the grain boundary etch groove 92 pass through the light integrating sphere 22 and reach the second photodetector 50. Substantially all of the etch pit scattered light 30 is captured in the light integrating sphere 22, as described above, and is detected only by the first photodetector 40. As a result, the signal produced by the second photodetector 50 is essentially the result of a grain boundary 90 in the area of illumination by beam 18. This signal on lead 52, therefore, can be processed, discriminated, and used for detecting and mapping grain boundaries in polycrystalline materials as distinct from dislocation defects.

In FIG. 2 the light components 34, 36, and 38 that pass through the top aperture 24 of light integrating sphere 22 are collimated by a lens 114, reflected out of the normal path by beam splitter or partially silvered mirror 116, and directed to the center block aperture 44. As mentioned above, the projected light components 34, 36, and 38 and which forms spots 100, 101, 102 that reach plane 112 of aperture 44 are substantially as shown in FIG. 6. The aperture 44 has an annular opening 45 large enough to pass substantial portions of the near specular components 34 and 36 and a center block 46 large enough to block the specular light component 38. The convex lens 48 converges and focuses the near 38 specular light components 34 and 36 onto the second detector 50, so that the projection of the light, essentially comprising the near specular light components 34 and 36, appears as the near spots 101 and 102, illustrated in FIG. 7, without the specular light component 38 and circular center spot 100. It is important to eliminate the specular light component 38, because a substantial portion of the specular light component 38 can be, and probably is, light reflected from smooth, nondefect areas of the surface 20 of the polycrystalline material 14 adjacent the grain boundary 90, thus could also be present in the signal from the second photodetector 50, even if there is no grain boundary in the area of illumination. Elimination of the central or specular light component 38 insures that the only signal from photodetector 50 is from a grain boundary defect.

It may be noted that the more diverse components of the grain boundary scattered light 94 that produce the intermediate spots 103–108 in the pattern 98, as illustrated in FIGS. 4a, 4b, and 5, will not pass through the top aperture 24 of light integrating sphere 22, thus will be captured along with the etch pit scattered light 30 inside the light integrating sphere 22 of FIG. 2. If those intermediate components of the grain boundary scattered light 94 are intense enough, they can affect and cause erroneous signals of etch pit density (EPD) from the first photodetector 40. In fact, if the beam 18 was narrowed to a point, and if the point was focused on the grain boundary etch 92, the resulting grain boundary scattered light 94 intensity inside the light integrating sphere 22 would probably predominate and could even swamp out any etch pit scattered light intensity. Actually, the first photodetector 40 could operate as a grain boundary 90 detector in that configuration.

On the other hand, the effect of the intermediate components of grain boundary scattered light 94 can be minimized in several ways. First, the incident beam 18 can be operated with a wide diameter, thus illuminating a larger area of etch pit defects 70 on the surface 20 of the polycrystalline material 14. Such wide area illumination increases substantially the intensity of etch pit scattered light 30 inside the light integrating sphere 22 as compared to the grain boundary scattered light 94. Further, since the problem of the grain boundary scattered light 94 is essentially one dimensional, while the pattern of the etch pit scattered light 30 is two dimensional, a larger area illumination can minimize the effect of the grain boundary scattered light 94 inside the light integrating sphere 22 that is detected by the first photodetector 40. Additional electronic signal conditioning and processing, as described below, can further minimize the residual effects of the grain boundary scattered light 94 detected by first photodetector 40.

Another adjustment that can minimize the effects of diverse components of grain boundary scattered light 94 is to increase the distance between the bottom aperture 26 of the light integrating sphere 22 and the surface 20 of the polycrystalline material 14. Increasing this distance can allow the furthest-out components of the grain boundary scattered light 94, which spread at a large angle to normal, i.e., a smaller angle to the surface 20, to pass beneath the light integrating sphere 22 and avoid capture by the bottom aperture 26. Of course, raising the light integrating sphere 22 to an even larger distance off the surface 20 could cause the outer fringes of the etch pit scattered light 30 to be excluded, too, which could be counterproductive. Widening the bottom aperture 26 along with increasing the distance between the light integrating sphere 22 and the surface 20 could help to capture the outer fringes of the etch pit scattered light 30, but wider apertures can also allow diffuse light inside the light integrating sphere 22 to escape, thus lowering intensity and signal strength from the first photodetector 40. Therefore, there is a balance that can be found and maintained between incident beam 18 size, distance between light integrating sphere 22 and surface 12, and sizes of apertures 24 and 26 that provides optimum results and signals for a particular system 10 used in conjunction with a particular polycrystalline material 14. A larger beam 18 size can also increase the size of the raster increments needed to scan a sample 14 as well as increasing the statistical base of the method used in this invention, which detects statistical defect densities instead of detecting and counting individual etch pits. Therefore, the larger raster increments along with the increased statistical base of defect densities that result from a larger sized beam 18, as described above, can combine to increase substantially the defect mapping speed and efficiency according to this invention.

Referring again to FIG. 1, the etch pit density (EPD) signal on lead 42 is directed to a first amplifier circuit 120, where it is conditioned, filtered, cleaned up, and amplified. Likewise, the grain boundary signal on lead 52 is directed to a second amplifier circuit 122, where it is also conditioned, filtered, cleaned up, and amplified. Both signals are then directed via leads 124, 126, respectively, to an algebraic summing circuit 128, where the etch pit or dislocation signal is algebraically summed with (subtracted from) the product of an empirically determined constant times the grain boundary signal to produce a new signal that is indicative of grain boundary for mapping purposes. Initialization can be made on a location that is known to be all dislocation defects and no grain boundary defects. In the opposite mode, the grain boundary signal can be algebraically summed with the product of a constant times the dislocation signal to produce a net signal that is indicative of dislocation density.

The dislocation density and grain boundary signals are fed into a computer 130 along with X-Y position information from the stage 12 via connection 132. The data is stored in a high-speed buffer memory. Commercially available computer software, such as "Lab View," produced by National Instruments, of 6504 Bridgepoint Parkway, Austin, Tex. 78730, and "Delta Graph," produced by Deltapoint, Inc. of 2 Harris Court, Suite B-1, Monterey, Calif. 93940, can be used, with appropriate modifications for particular system hardware and other parameters that would be within the capabilities of persons skilled in this art, to make a map of the dislocation densities and grain boundaries in the material 14, and detailed analysis or displays can be made on the monitor 134 and by a color printer or plotter 136. For example, a defect density map produced with the system 10 according to this invention is shown in FIG. 9. Alternatively, the grain boundary data can be used to produce a grain boundary map. For example, the grain boundaries shown in the microscopic photograph of FIG. 10a was scanned with the system 10 of this invention, and the grain boundary map in FIG. 10b was produced with the data. Alternatively, analog signals from the photodetectors 40 and 50 can be processed by the analog display controller 138 to directly display the dislocation and grain boundary distributions on a storage oscilloscope 140 or an X-Y recorder 142.

The preferred etching process for use with this invention is a variation of the chemical etching procedure published by the inventor in B. L. Sopori, "A New Etch for Polycrystalline Silicon," *J. Electrochem*,: SOLID-STATE SCIENCE AND TECHNOLOGY, Vol. 131, No. 3, Page 667 (1984), which produces substantially equal volume etch pits, regardless of dislocation orientation, which is incorporated herein by reference. The following mixtures are used in defect etching:

1) 1:1 of hydrofluoric acid (I-IF) to water, referred to as the HF rinse.

2) 1:1 of nitric acid ($HNO_3$) to water, referred to as the $HNO_3$ rinse.

3) 36:15:2 of hydrofluoric acid to acetic acid ($CH_3COOH$) to nitric acid, referred to as Sopori etch.

4) 2:1 of sulfuric acid ($H_2SO_4$) to hydrogen peroxide ($H_2O_2$), referred to as Piranha.

The steps of this procedure include:

a) Make sure the sample to be etched is clean by checking it under the microscope. If the sample is not clean (there are blobs visible on the surface), it should be cleaned.

b) Heat the Piranha on a hot plate (not shown) to 80° C. (a setting of "LOW"). It should take approximately 15–20 minutes to heat the Piranha. It is hot enough when it begins to gently bubble. Do not let the Piranha reach a full boil. If the Piranha was just mixed it does not need to be heated; the heat generated in mixing the $H_2SO_4$ and $H_2O_2$ is adequate.

c) Place the sample in a Teflon sample holder and then let the sample sit in the Piranha for 15 to 30 minutes. The Piranha cleans off any remaining small bits of wax or dirt on the surface of the sample. After the sample has soaked, rinse it off with a stream of deionized (DI) water and blow it dry with an air gun (not shown).

d) The HF rinse, the $HNO_3$ rinse, and the etch should be poured into separate, labeled, plastic one-liter beakers. Fill a two-liter beaker with DI water for rinsing the samples after etching.

e) Dip the sample into the etch and gently wave it back and forth for approximately 30 seconds after bubbles begin to form. Remove the sample from the etch and immediately dip it into the beaker of DI water. Gently wave the sample back and forth for several seconds and then risen it with a stream of DI water. Dry the sample with the air gun.

f) Dip the sample in the $HNO_3$ rinse and gently wave it back and forth for approximately 15 seconds. Remove the sample and dip it into the beaker of DI water for several seconds. Rinse the sample in a stream of DI water and then dry it with the air gun.

g) Dip the sample in the HF rinse and wave it back and forth for approximately 15 seconds. Remove the sample and dip it into the beaker of DI water for several seconds. Rinse the sample in a stream of DI water and then dry it with the air gun.

A second embodiment system 200 is shown in FIG. 11. In this embodiment, the light integrating sphere 22 is positioned far enough away from the surface 20 to accommodate the collimating lens 114 and beam splitter 116 between the light integrating sphere 22 and surface 20. The beam splitter 116 diverts part of the grain boundary scattered light 96 and etch pit scattered light 30 toward the second photodetector 50 before reaching the light integrating sphere 22. In this embodiment, the blocking aperture 244 passes only the outer portions 210 and 212 of the grain boundary scattered light 96 to the second detector 50 and blocks everything else. The bottom aperture 26 of light integrating sphere 22 is large enough to admit the etch pit scattered light 30, but small enough to block the outer portions of grain boundary scattered light 96 that passes through beam splitter 116. The near specular portions 34 and 36 of grain boundary scattered light 96 that pass through the beam splitter 116 also pass out the aperture 24 of light integrating sphere 22. Therefore, it is only the intermediate portions of grain boundary scattered light that enter and are captured in the light integrating sphere 22 along with the etch pit scattered light 30. These intermediate portions of grain boundary scattered light, as in the embodiment 10 described above, are not sufficient to swamp or degrade the intensity signal for etch pit scattered light 30 as long as the incident beam 18 illuminates a wide enough area on surface 20.

A third embodiment of a system 300 is shown in FIG. 12. The system 300 is similar to the system 10 shown in FIG. 1 with like components referenced with a prime designation A first laser 16' provides a beam 18' of light at a relatively long wavelength, preferably greater than 8000 Å, for example approximately 9000 Å. A second laser 302 provides a beam 306 of light at a wavelength different from the first laser 16', preferably less than 7000Å, for example 6382 Å. A lens 304 establishes the width of the beam 306 from the second laser 302. A lens 308 establishes the width of the beam 18' from the first laser 16'. A beam splitter 310 is placed between the light integrating sphere 22' and the first laser 16' in such a position as to allow the beam 306 from the second laser to be positioned substantially parallel with the beam 18' from the first laser 16' and directed toward the crystalline material or sample 14'. The beam splitter 310 has a central portion 311 which is reflective while the remaining portion is not. Consequently, the specular portion of the light reflected from the surface 20' of the material 14' is reflected back toward the second laser 302 while the near specular light components 34' and 36' pass by the beam splitter 310 and are directed to the second photodetector 50'.

A signal 312 is provided from the first laser 16' to the computer 130' containing information related to the total transmitted power in the beam 18'. Similarly, the second laser 302 provides a signal 314 to the computer 130' containing information related to the total transmitted power in the beam 306.

A third photodetector 316 is positioned in the opposite side of the light integrating sphere 22' from the first photodetector 40'. A first filter 318 is positioned in front of the first photodetector 40' to allow reflected light from laser beam 18' to pass therethrough but with transmission characteristics which cause reflected light from laser beam 306 not to pass therethrough. Similarly, a second filter 320 is positioned in front of the third photodetector 316 and allows reflected light from laser beam 306 to pass therethrough while blocking reflected light from laser beam 18'. The third photodetector 316 produces a signal 322 indicative of the intensity of the diffused light 32' which is of the wavelength of laser beam 306. This signal 322 is transmitted to the signal processing and control unit 60' where a third amplifier circuit 324 conditions, filters, cleans-up and amplifies the signal 322 before supplying a third amplified signal 326 to the analog display controller 138' and the computer 130'.

The lens 304 is chosen so that the beam 306 is preferably of a width similar to the width of a grain boundary etch, or 0.1 mm. This relatively small beam width produces a sharper grain boundary definition since the sharpness of the grain boundary image is determined by the convolution of the grain boundary groove size and the beam width. The lens 308 is chosen so that the beam 18' is preferably in the range of 0.5–1.0 mm to provide a sufficient statistical sample of dislocation defects. In this way, this embodiment can be optimized separately for each of the type of defects rather than selecting a compromise beam width.

The use of two light beams, each having a different wavelength, provides another advantage. Namely, variations in the size of the etch pits can be corrected for by the use of the dual wavelength system. The variations can occur from variations in the time duration of the etching process or the exact composition and cleanliness of the etchant solution. FIG. 13 shows graphs of the normalized signal received from the diffuse light reflected off the material 14' as a function of etch pit density. It can be seen that this function is also dependent on the etch pit size and the wavelength of the light. Curve 400 shows the relationship between the etch pit density and the normalized signal, with a first etch pit size and a relatively long wavelength. Curve 402 shows the relationship, with the first etch pit size and a relatively shorter wavelength. At a particular etch pit density 403, a difference 404 or a ratio can be calculated between the curve 400 and the curve 402.

Curve 406 shows the relationship between the etch pit density and the normalized signal, with a second etch pit size (which is larger than the first) and the relatively long wavelength. Curve 408 shows the relationship, with the second etch pit size and the relatively shorter wavelength. At the same particular etch pit density 403, a difference 410 or a ratio can be calculated between the curve 406 and the curve 408. It can be seen that the difference 410 is smaller than the difference 404. This relationship between the differences 404 and 410 can be exploited to determine and correct for variations in etch pit size.

It is also possible to obtain maps of reflectance and photoresponse for a photovoltaic device or solar cell (also referenced as 14') which has been produced from crystalline material 14'. With the system 300 (FIG. 12) the signals from the photodetectors are summed to obtain total reflectance. By translating the X-Y table 12', a reflectance map can be produced. Maps of diffuse, specular, and total reflectance can be produced for each wavelength produced by the lasers 16' and 302. To perform light beam induced current (LBIC) measurements on the photovoltaic device 14' the light integrating sphere 22' is mounted in such a manner as to allow it to be moved laterally away from the X-Y translation stage or table 12'. A pair of electrical leads 328 and 330 are attachable to opposite sides of the photovoltaic device 14'. The leads 328 and 330 are also connected to the respective input terminals of a low-input-impedance amplifier 332 which supplies a signal 334 to the analog display controller 138' and the computer 130' indicative of the current flowing through the leads 328 and 330 and the photovoltaic device 14'.

The reflected power is subtracted from the total transmitted power as communicated by the signal 312 to the computer 130'. From this difference, the total absorbed power (by the photovoltaic device 14') can be calculated. The current induced through the device 14' by the incoming light is measured by the amplifier 332 and an optical energy-to-electrical energy conversion efficiency (photoresponse) can be calculated. These calculations can be repeated as the material 14' is rastered by the X-Y table 12' so as to create a two-dimensional "map" of photoresponse. External photoresponse is a measure of the electrical power produced as a function of the total transmitted optical power. Internal photoresponse is a measure of the electrical power produced as a function of the total absorbed optical power.

Dual wavelengths provide several advantages to the LBIC measurements. The longer wavelength light tends to penetrate deeper into the material 14' than the shorter wavelength light, and thus the longer wavelength light can be used to provide information about the property of the material such as the minority carrier diffusion length. This parameter is the length an electron (which is the minority carrier in P-type material) can go toward the N-P junction without combining with a hole. On the other hand, the shorter wavelength light provides information relating to the near-surface features of the material 14'. These features may include grain boundaries and N-P junction characteristics. It is important to examine the nonuniformities in the material or photovoltaic device because the inefficient portions of the material are a sink to the power generated by the more efficient portions of the material. The nonuniformities may be due to the growing process, other defects, the junctions or the anti-reflective coating on the material.

Among the many possible alternatives which could be used in the above-described embodiments are the substitution of a non-laser light source for the laser. The light source need not be coherent. However, with the third embodiment it is desirable for the light source to have a relatively narrow color output. In addition, it would be possible to use mirrors or a separate light source to provide the beam for LBIC to a remote section of the material 14' as an alternative to moving the light integrating sphere 22'.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to failing within the scope of the invention as defined by the claims which follow.

The embodiments of the invention in which an exclusive property or privilege is claimed are defined as follows:

1. A method for detecting and distinguishing between a first type of defect and a second type of defect in a surface of a crystalline material, comprising the steps of:

preparing the surface in such a manner that the first type of defect scatters incident light in a first pattern and the second type of defect scatters incident light in a second pattern;

illuminating the surface with incident light of both a first color and a second color to create the first pattern of scattered light and the second pattern of scattered light;

separating the first pattern of scattered light from the second pattern of scattered light;

detecting the scattered light of the first pattern as an indication of the first type of defect in the surface of the crystalline material; and detecting the scattered light of the second pattern as an indication of the second type of defect in the surface of the crystalline material.

2. A method as defined in claim 1, wherein the illuminating step includes incident light of the first color being provided in a beam of relatively narrow width and incident light of the second color being provided in a beam of relatively wider width.

3. A method as defined in claim 1, wherein the illuminating step includes the first color of incident light being of a relatively shorter wavelength than the second color of incident light.

4. A method as defined in claim 1, wherein the illuminating step includes providing a first laser for supplying the first color of incident light and a second laser for supplying the second color of incident light.

5. A method as defined in claim 1, wherein the first type of defect includes dislocation defects in the crystalline material and the second type of defect includes grain boundaries in the crystalline material.

6. A method of measuring characteristics of a piece of material, wherein the piece of material includes a photovoltaic device, comprising the steps of:

exposing the piece of material to incoming light of a known level of power;

determining the power level of the light reflected from the piece of material;

calculating the amount of light absorbed by the piece of material based upon the power level of the light exposed and the power level of the light reflected; and measuring the electrical current induced through photovoltaic device by the incoming light.

7. A method as defined in claim 6 further including the step of:

varying the position of the piece of material relative to the incoming light;

wherein the calculating step includes calculating the amount of light absorbed by the particular position of the piece of material.

8. A method as defined in claim 7, wherein the varying step is performed in a raster pattern to create a map of characteristics by the calculating step.

9. A method as defined in claim 8, further including the step of:

creating a reflectance map from the determination of power reflected.

10. A method as defined in claim 6, further including the step of:

calculating the efficiency of the photovoltaic device based upon the amount of light absorbed by the device and the electrical current induced therethrough by the light.

11. A method as defined in claim 6 wherein the exposing step includes utilizing light of a wavelength less than 700 Å to measure absorption characteristics relating to features in the interior of the piece of material.

12. A method as defined in claim 6 wherein the exposing step includes utilizing light of a wavelength greater than 800 Å to measure absorption characteristics relating to features in the interior of the piece of material.

13. An apparatus for measuring characteristics of a piece of material by determining the response of the piece of material to a beam of exposed light from a light source, comprising:

means for providing the beam of light from the light source to the piece of material;

a support to which the piece of material is mounted;

means for varying the position of the beam of light relative to the piece of material and for supplying a position signal relating to the relative position;

an optical light integrator mounted adjacent to the piece of material to receive a substantial amount of the light reflected from the piece of material at angles not normal to the surface of the piece of material;

means associated with the optical light integrator for measuring the quantity of light received by the optical light integrator, and for supplying an off-axis signal related thereto;

means operatively connected to the apparatus for receiving the light which is reflected at angles substantially normal to the piece of material;

means associated with the normal-angle receiving means for measuring the quantity of light received thereby and for supplying an on-axis signal related thereto;

means receptive of the position signal, the off-axis signal and the on-axis signal, for reporting information related thereto.

14. An apparatus as defined in claim 13, wherein the light source includes a laser.

15. An apparatus as defined in claim 13, wherein the support and the position varying means includes an X-Y platform on which the piece of material is supported and which can be controlled to vary the two-dimensional position of the piece of material relative to the light beam.

16. An apparatus as defined in claim 13, wherein the optical light integrator is spherical and defines an upper and a lower aperture therein, with the lower aperture positioned adjacent the piece of material and the upper aperture aligned with the lower aperture to allow the light beam to pass through the upper and lower apertures, further wherein the normal-angle receiving means is positioned to receive light which is reflected from the piece of material and passes back through the lower and upper apertures.

17. An apparatus as defined in claim 13, wherein the normal-angle receiving means includes a beam splitter which allows the light beam from the source of light to pass therethrough and reflects the light reflected from the piece of material toward the light measuring and on-axis signal supplying means.

18. An apparatus as defined in claim 17, further including:
a light block which defines an annular aperture, the block being located between the beam splitter and the light receiving and on-axis signal supplying means to block the light which is precisely on-axis and allow the light which is nearly on-axis to pass therethrough.

19. An apparatus as defined in claim 13, wherein the light measuring and off-axis signal supplying means and the light measuring and on-axis signal supplying means each include a photodetector.

20. An apparatus as defined in claim 13, wherein the reporting means includes a computer.

21. An apparatus as defined in claim 13, wherein the reporting means includes a display controller.

22. An apparatus as defined in claim 13, further including:
means for providing a second beam of light, the light having a wavelength different from the wavelength of the light source providing the first beam of light;
means for directing the second beam of light to a position parallel to the first beam of light to allow each beam to be provided to the piece of material; and
means associated with the optical light integrator for measuring the quantity of light of the different wavelength received by the optical light integrator and for supplying a second color off-axis signal related thereto;
wherein the reporting means is receptive of the second color off-axis signal.

23. An apparatus as defined in claim 22, wherein the light source provides light of a first wavelength and wherein the light measuring and off-axis signal supplying means measures the light of the first wavelength and not of the different wavelength and the off-axis signal supplied is a first color off-axis signal.

24. An apparatus as defined in claim 23, wherein the first beam has a diameter substantially different in size than the second beam so that the larger beam can be employed to detect a first type of defect in the piece of material and the smaller beam can be employed to detect a second type of defect in the piece of material.

25. An apparatus as defined in claim 13, wherein the optical light integrator is movably mounted adjacent the piece of material so that the integrator can be moved away from the piece of material, and wherein the piece of material includes a photovoltaic device, and further including:
means for sensing the electrical current flowing through the photovoltaic device and supplying a current signal related thereto.

* * * * *